United States Patent
Ninomiya et al.

(10) Patent No.: US 6,778,849 B1
(45) Date of Patent: Aug. 17, 2004

(54) BODY PROBE FOR MRI AND MRI DEVICE

(75) Inventors: Atsushi Ninomiya, Ome (JP); Ryosuke Fukami, Atsugi (JP); Isamu Takekoshi, Tokyo (JP); Tsuneo Maeda, Tokyo (JP); Shizuka Nagai, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/937,849

(22) PCT Filed: Mar. 30, 2000

(86) PCT No.: PCT/JP00/02013

§ 371 (c)(1),
(2), (4) Date: Nov. 15, 2001

(87) PCT Pub. No.: WO00/57782

PCT Pub. Date: Oct. 5, 2000

(30) Foreign Application Priority Data

Mar. 31, 1999 (JP) .......................................... 11/092908

(51) Int. Cl.⁷ .............................................. A61B 5/055
(52) U.S. Cl. ...................................... 600/422; 324/318
(58) Field of Search ................................. 600/410, 421, 600/422; 324/318, 322

(56) References Cited

U.S. PATENT DOCUMENTS 5,351,688 A * 10/1994 Jones .......................... 600/422
5,519,321 A *  5/1996 Hagen et al. ................ 600/422

* cited by examiner

*Primary Examiner*—Ruth S. Smith
(74) *Attorney, Agent, or Firm*—Antonelli, Terry, Stout & Kraus, LLP

(57) ABSTRACT

A body probe for MRI has a base coil portion, two side coil portions to be connected to side-coil connecting portions provided on both sides of the base coil portion, and a center coil portions which connects the two side coil portions at the center of the chest of the subject. Each side coil portion is made of a soft member and has a flexible coil embedded inside, so that the side coil portion can have a shape which matches the side surface of the subject. Provided at the center of the two side coil portions which are to be connected to the center coil portions at the chest of the subject is a fixing band for fixing the side coil portions and the center coil portion in close contact with the subject.

11 Claims, 12 Drawing Sheets

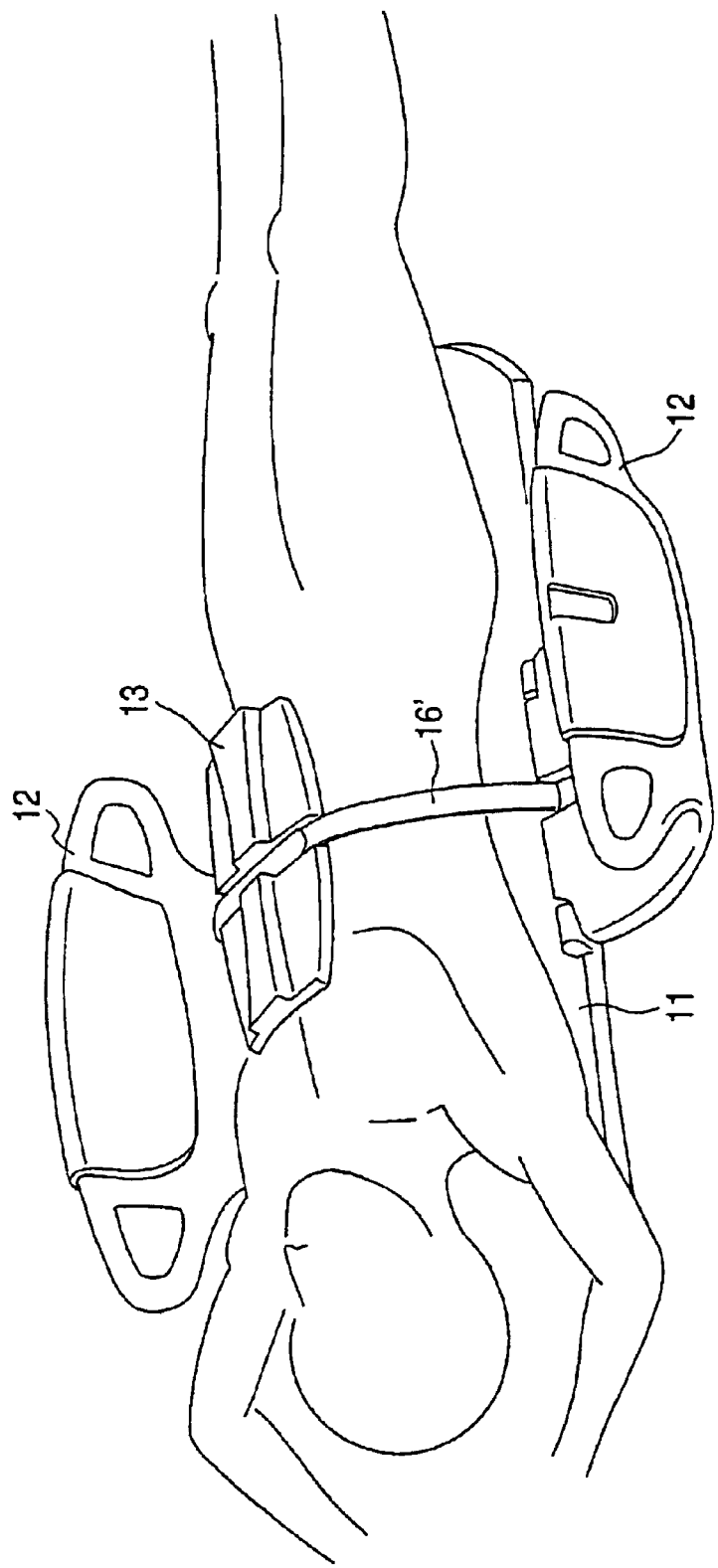

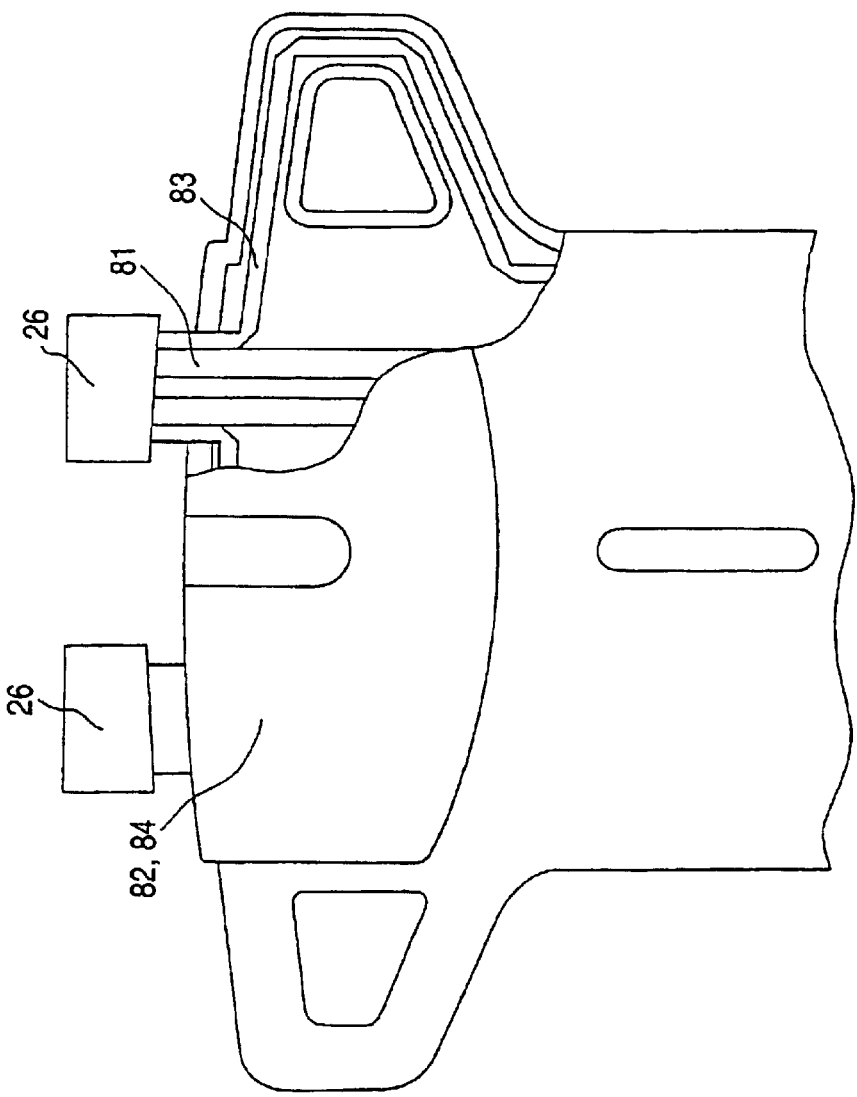

BODY PROBE FOR MRI AND MRI DEVICE

BACKGROUND OF THE INVENTION

The present invention relates to a body probe for MRI and an MRI apparatus using the probe; and, more particularly, the invention relates to a body probe for MRI, which is easy to use and provides clear images without image degradation, and an MRI apparatus using the probe.

In general, a body probe for MRI comprises two reception coils that are to be positioned above and under a subject to be examined (examinee). A typical body probe for MRI has upper and lower coils formed integrally into a cylindrical shape or a cylindrical shape which can be partly opened sideways, or a belt-like shape.

FIGS. 11A and 11B are diagrams which show one structural example of a body probe for MRI. Referring to the figures, "111" denotes a body probe, "112" denotes a body portion and "113" denotes a window. The body probe 111 exemplified in FIGS. 11A and 11B has a cylindrical shape.

As shown in FIG. 11A, the body probe 111 comprises a cylindrical body portion 112 which has a length and internal vertical and horizontal sizes that are long and large enough to cover the chest of a subject to be examined. The windows 113 are formed in the top and bottom portions on both sides of the body portion 112 in order to lighten the overall weight of the body probe and permit the position of the subject with respect to the body probe to be checked from the outside. Though not illustrated, reception coils are embedded in the body portion 112 and are connected to an MRI apparatus, so that signals from the coils can be processed to form an image to be displayed.

FIG. 11B shows how the cylindrical body probe 111 is used. A subject to be examined, whose chest is enclosed by the body probe 111, is placed inside an MRI apparatus for examination. Generally speaking, the size of a person's chest varies from one person to another. It is therefore difficult to prepare a probe which precisely matches the size of the chest of each subject, and such an attempt inevitably results in an increase in the cost of the entire MRI system. For this reason, normally, three or so different sizes of body probes 111 are prepared and used for all subjects of different builds.

Although the body probe exemplified in FIGS. 11A and 11B is designed to be completely cylindrical, there is a body probe designed in such a way that it can be opened sideways at the center portion.

FIG. 12 is a diagram showing another structural example of a body probe for MRI. In FIG. 12, "121" denotes an opening, "122" denotes an upper coil, "123" denotes a lower coil, "124" denotes a belt, "125" denotes cords, and "126" denotes a connector box.

The body probe for MRI exemplified in FIG. 12 has reception coils, which comprise the upper coil 122 and the lower coil 123. In using the body probe, the lower coil 123 and the upper coil 122 are secured by the belt 124. The lower coil is placed under the back of a subject to be examined and the upper coil is placed over the abdominal portion, the chest or the like of the subject. The belt 124 is attached to a belt groove provided in the frame of a bed in such a way as to be movable along the bed to secure the subject at a desired portion. The belt 124 is movable in accordance with the mounting position of the upper coil 122. The body probe for MRI which has the above-described structure can securely fix the upper coil 122 and the subject together.

The cords 125 that extend from the upper and lower coils run along one edge portion of the bed and are connected to the connector box 126 located inside the opening 121 of the MRI apparatus. At the time of picking up an image with the MRI apparatus, the subject is moved into the opening 121 to a predetermined position together with the top table of the bed and the connector box 126.

The cylindrical body probes for MRI as described above do not have fixed distances between the subject and the coils in the body probe due to a difference in the build of the subject, and difficulty is experienced in securing the subject inside the body probe. This makes the characteristics of the coils unstable, so that picked-up image of the subject is degraded by movement of the body of the subject. The cylindrical body probe also has a shortcoming in that it is not easily attached to a subject.

Another body probe for MRI, whose reception coils comprise an upper coil and a lower coil, has no coil portions provided at portions corresponding to the sides of the subject. In addition, it is difficult to place the center of the upper coil over the center of the body axis of the subject, so that the center of the upper coil may be misaligned with respect to the center of the body axis of the subject. This makes it difficult to acquire clear images.

With regard to use of a belt-like body probe, one among several sizes of body probes which matches the build of a subject to be examined is selected and is fitted on the subject. This type of body probe cannot restrain movement of the body of the subject, so that the body probe moves as the body of the subject moves. This also leads to image degradation.

The reception coils of the above-described body probes are cylindrical or belt-like and their sizes are not prepared subject by subject. Rather, one among several sizes of available body probes previously prepared, which is closest to the build of a subject to be examined, is selected. As the shapes of the reception coils become closer to the shape of the subject, the sensitivity becomes higher. To achieve a high sensitivity, therefore, it is necessary to fit the reception coils closely to the subject. On the contrary, the reception coils of the body probes of the type described above are difficult to fit closely to each subject to be examined.

SUMMARY OF THE INVENTION

Accordingly, it is an object of the present invention to provide an easy-to-use body probe for MRI, which is able to overcome the aforementioned problems, is easily attached to various subjects to be examined who have builds of different sizes and does not suffer image degradation, and an MRI apparatus which uses this probe.

The foregoing object is achieved by designing a body probe for MRI having reception coils for picking up an image for use in an MRI apparatus in such a way that the reception coils are provided in a center coil portion and two side coil portions.

The foregoing object is achieved by providing slide mechanisms for the side coil portions, which are formed by smooth surfaces, that are formed on both right and left sides of the center coil portion, at joint portions between the center coil portion and the side coil portions.

The foregoing object is achieved by designing a bottom surface of the center coil portion to have a curved shape, or providing an indicator indicating the center of the center coil at the center of a top surface of the center coil portion. The indicator indicating the center of the center coil may be a groove, a projection or a line drawn in a color different from the color around the line.

The foregoing object is also achieved by designing a body probe for MRI having reception coils for picking up an image for use in an MRI apparatus in such a way that the reception coils are provided in a center coil portion, side coil portions and a base coil portion. The center coil portion, the side coil portions and the base coil portion may be constructed independently of one another.

The foregoing object is achieved by constructing the side coil portions by embedding a flexible coil in a soft member, or by providing the side coil portions with cutaway holes at portions where there are no coil portions.

Other objects and structures of the invention and the resulting advantages thereof will become apparent from the following detailed description of an embodiment of the invention.

BRIEF DESCRIPTION OF THE DRAWINGS

FIG. 6 is a perspective view illustrating another means for fitting the center coil portion on the subject;

FIG. 8 is a diagram illustrating the shape of a coil formed in a side coil portion;

DESCRIPTION OF THE PREFERRED EMBODIMENTS

A preferred embodiment of the invention will be described below with reference to the accompanying drawings.

Figure 1:
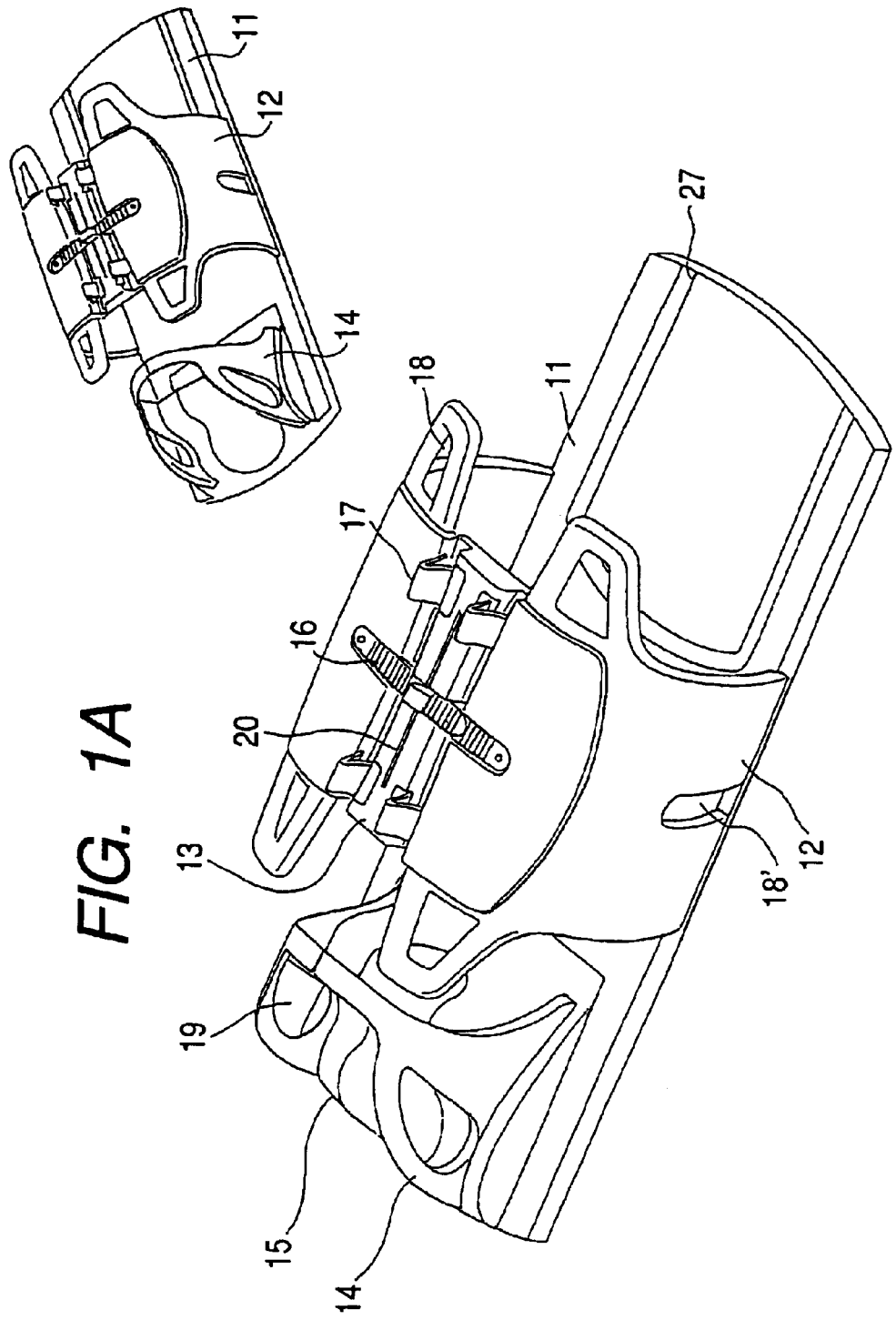
FIGS. 1A and 1B are perspective views showing the outward appearance of a body probe for MRI according to one embodiment of the invention.
Figure 2:
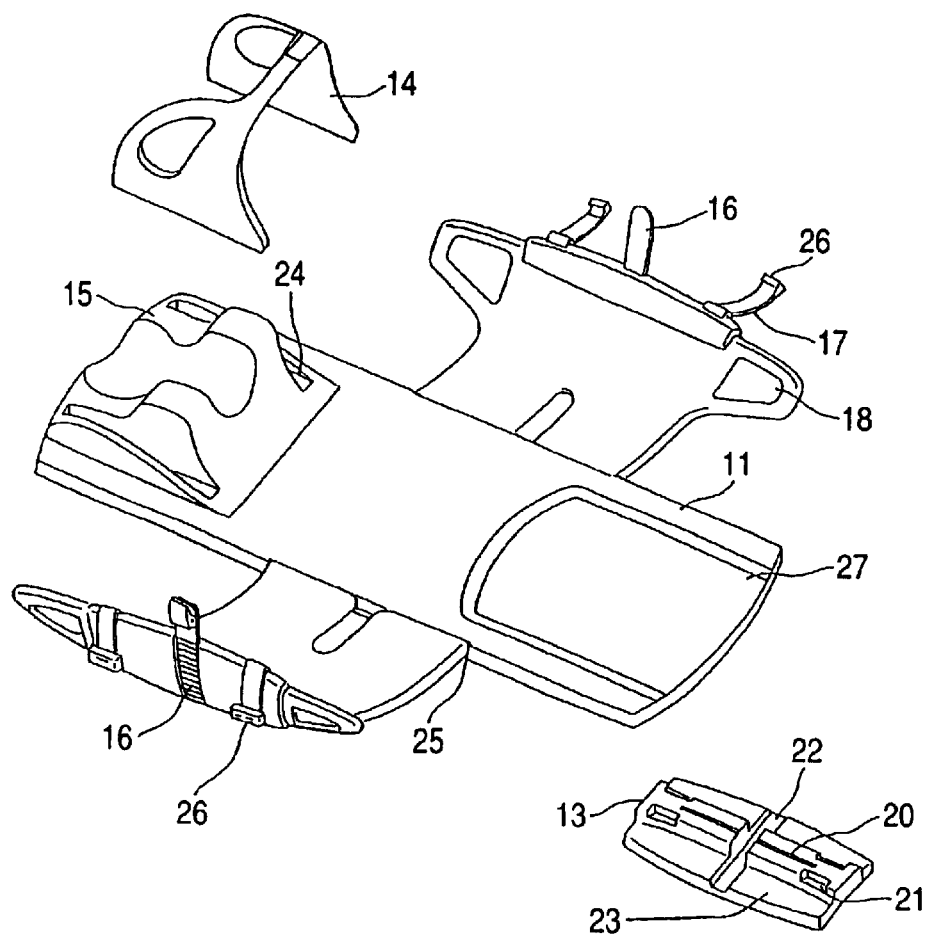
FIG. 2 is an exploded perspective view showing side coil portions of the body probe for MRI according to the embodiment of the invention opened.

FIGS. 1A and 1B are perspective views showing the outward appearance of a body probe for MRI according to one embodiment of the invention, and FIG. 2 is a diagram showing the side coil portions of the body probe according to the embodiment of the invention in the opened condition. In the drawings, the body probe has a base coil portion 11, a side coil portion 12, a center coil portion 13, a head coil portion 14, a head holder 15, a fixing band 16, a coil cable 16, cutaway holes 18 and 19, a center indicator portion 20, a cable connector 21, a fixing-band groove 22, a smooth surface 23, a head-coil connecting portion 24, side-coil connecting portions 25, a connector 26 and a recess portion 27.

As shown in FIGS. 1A and 1B (which are perspective views from different viewpoints that will not be distinguished from one another in the following description) and FIG. 2, the body probe for MRI according to the embodiment of the invention comprises a base coil portion 11, which is positioned at the back portion of a subject to be examined (hereinafter simply referred to as the "subject") when the person lays down on his or her back on an unillustrated bed, the two side coil portions 12, which are to be connected to the side-coil connecting portions 25 provided on both sides of the base coil portion 11, and the center coil portion 13, which connects the two side coil portions 12 at the center of the chest of the subject.

The head holder 15 is provided at that portion of the base coil portion 11 where the head of the subject is to be placed. The head holder 15 holds the head of the subject in such a way that the subject's head does move around. The recess portion 27 where the buttocks of the subject will rest is provided at the opposite side of the base coil portion 11 relative to the head holder 15. The side-coil connecting portions 25 are formed on both sides of the base coil portion 11, and the side coil portions 12 are to be attached in such a way as to be movable at an arbitrary angle with respect to the base coil portion 11. This design makes it possible to open the side coil portions 12, as shown in FIG. 2, to facilitate attachment of the body probe to the subject at the time of attachment. Further, folding the side coil portions 12 inside makes it easier to carry the side coil portions 12 around and can contribute to reducing the storage space therefor. The side coil portions 12 can be detached from the base coil portion 11 at the positions of the side-coil connecting portions 25.

Each side coil portion 12 is made of a soft member, such as a rubber-based or urethane based member, and has a band-like conductive member embedded inside. As will be discussed later, therefore, the side coil portions 12 can take shapes which match the side surfaces of the subject and can be fitted closely on the subject. Even when the subject puts weight on the side coil portions 12, the soft members used for the side coil portions 12 neither cause pain on the subject nor damage to the side coil portions 12. For the purpose of weight reduction, the cutaway hole 18 is formed in that portion of each side coil portion 12 where the internal coil does not exist. To improve the image quality, that portion of each side coil portion 12 which is to be connected to the center coil portion 13 is designed to be arcuately curved in such a way that the curved portion comes closest to the coil center of the base coil portion 11.

Two coil cables 17 having connectors 26 are provided on each side of those portions of the two side coil portions 12 which are to be connected to the center coil portion 13 at the chest of the subject. Provided at the center portions of those portions of the two side coil portions 12 which are to be connected to the center coil portion 13 at the chest of the subject are the fixing bands 16 for fixing the side coil portions 12 and the center coil portion 13 in close contact with the subject. A cutaway hole 18' is formed in each side coil portion 12 on the side close to the base coil portion 11. When the side coil portions 12 are fitted on the subject, portions of the subject can be seen through the cutaway holes 18'. The cutaway holes 18' also serve to improve the ventilation.

The center coil portion 13, which is to be placed at the center of the chest of the subject, has capabilities to couple the two side coil portions 12 together and electrically connect the coils in the coil portions. The center coil portion 13 improves the close attachment to the subject and always stays on the center of the body axis of the subject, so that the constant precision of picked-up images can be maintained. To ensure adequate coil shapes at the time the center coil portion 13 is connected to the side coil portions 12, the bottom surface of the center coil portion 13 is curved to match the shape of the chest of the subject. This design can reduce the sensation of pressure on the subject.

As shown in FIG. 2, the center coil portion 13 is provided with smooth surfaces 23 on the right and left sides, which constitute slide mechanisms. The center portion of the center coil portion 13 that is adjacent to the smooth surfaces 23 is a step portion which is thicker than the smooth surfaces 23. Provided at the step portion of the center portion are the cable connectors 21 to which the connectors 26 attached to the coil cables 17 of the side coil portions 12 are connected. The center indicator portion 20 that indicates the center is provided at the position of the center portion, which becomes the center of the body axis, as a groove, a projection or a line drawn in a color different from the color around the line. Further provided in the center portion of the center coil portion 13 in a direction perpendicular to the body axis is the fixing-band groove 22 through which the fixing bands 16 are bed.

The head coil portion 14 is suitable for use with the body probe according to the embodiment of the invention. The head coil portion 14, when in use, is coupled to the head-coil connecting portions 24 formed on both sides of the head holder 15. As will be discussed later, the cutaway holes 19 in the head coil portion 14 are provided at the positions of the ears of the subject so as to suppress the sensation of pressure at the time the head coil portion 14 is mounted on the subject and to permit smooth conversation with a caretaker.

Figure 3:
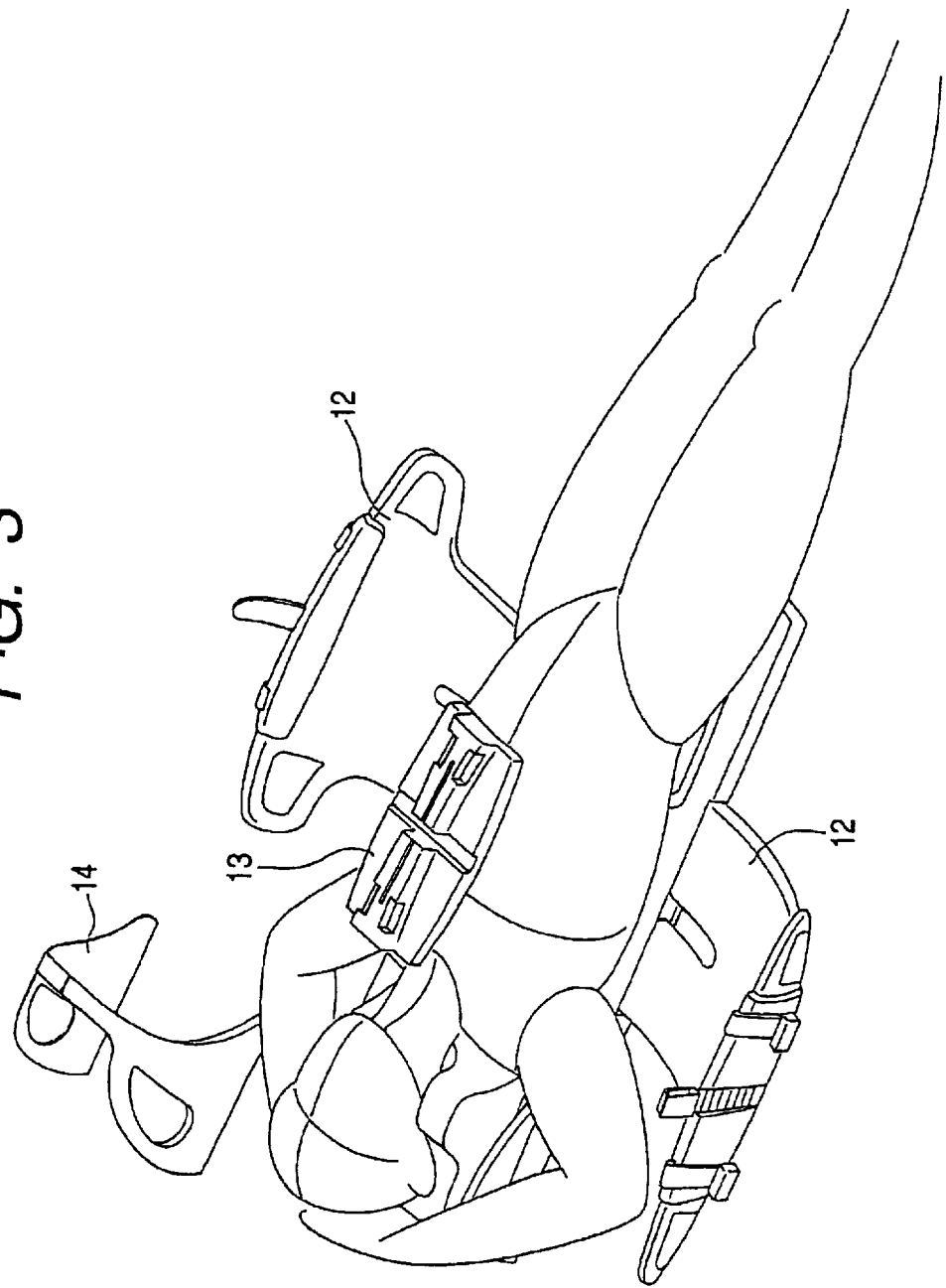
FIG. 3 is a perspective view illustrating the procedures of fitting the body probe according to the embodiment of the invention to a subject to be examined.
Figure 4:
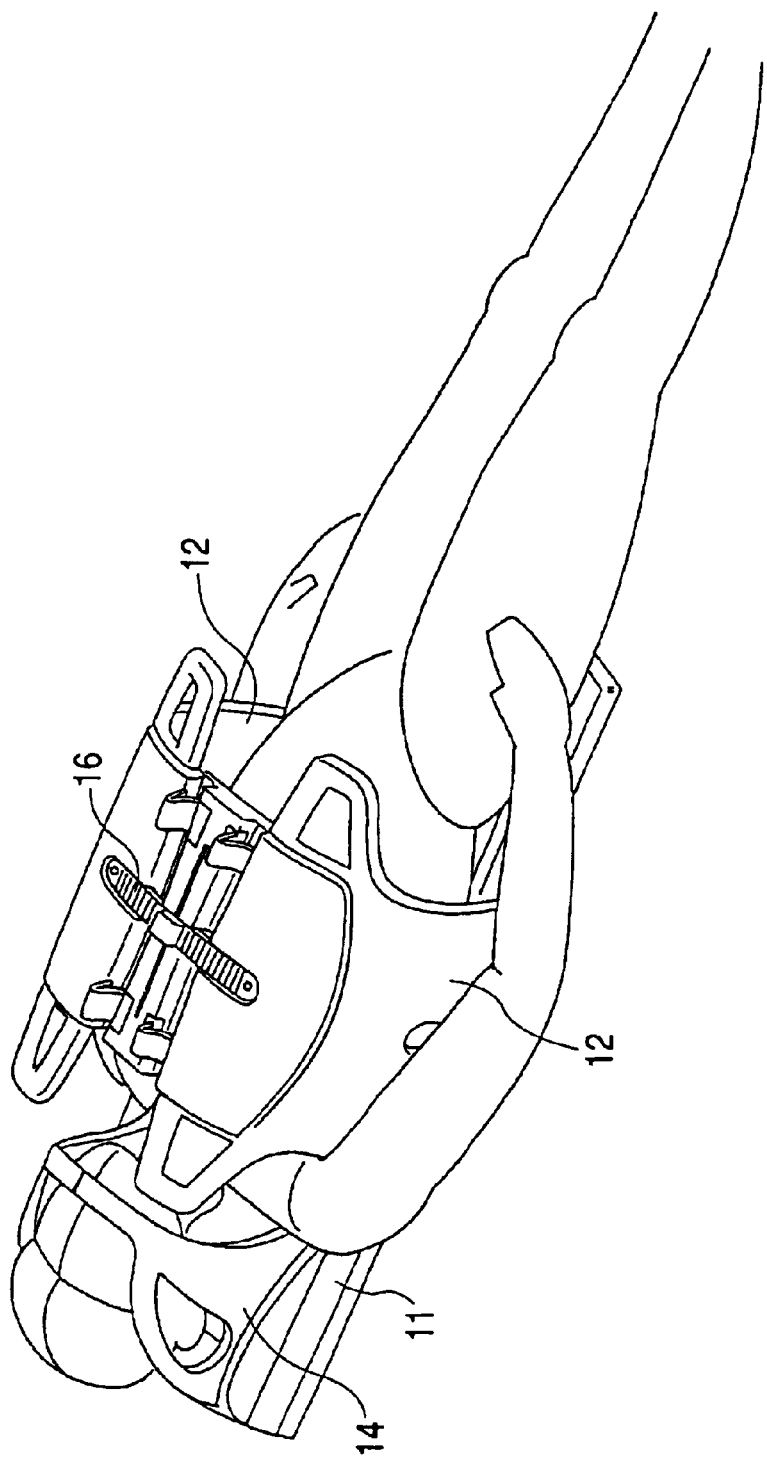
FIG. 4 is a perspective view illustrating the state in which the body probe according to the embodiment of the invention is fitted on the subject (examinee)
Figure 5:
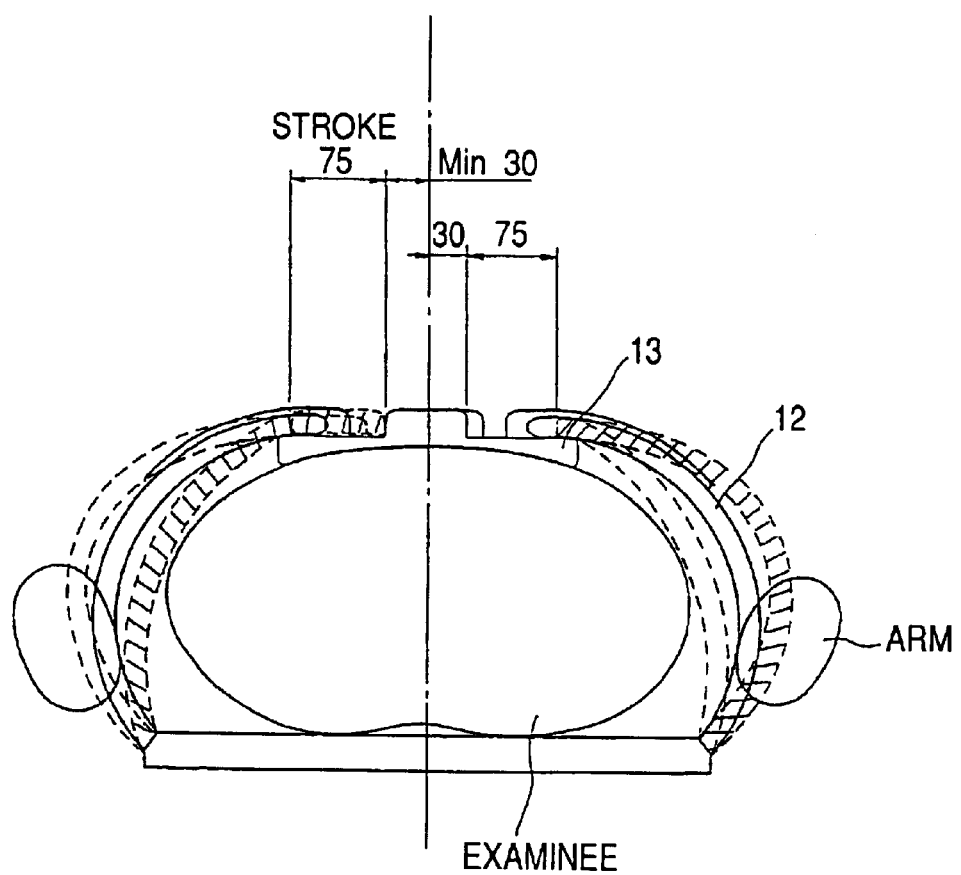
FIG. 5 is a cross-sectional diagram illustrating how the side coil portions are deformed.

FIG. 3 is a diagram illustrating the procedures involved in fitting the body probe according to the embodiment of the invention on a subject; FIG. 4 is a diagram illustrating the state in which the body probe according to the embodiment of the invention is fitted on the subject; and FIG. 5 is a diagram illustrating how the side coil portions are deformed. Referring now to FIGS. 3 to 5, the procedures used in fitting the body probe on the subject and the fitted state will be described below.

With the side coil portions 12 opened sideways and the head coil portion 14 removed, as shown in FIG. 2, the subject is laid down on the base coil portion 11 in such a way as to place the subject's head in a cavity of the head holder 15, as shown in FIG. 3. At this time, the buttocks of the subject are positioned in the recess portion 27 of the base coil portion 11. Next, the caretaker places the center coil portion 13 on the chest of the subject and adjusts its position in such a way that the center indicator portion 20 coincides with the center of the chest of the subject and the fixing-band groove 22 is aligned with the position of the fixing bands 16 of the side coil portions 12.

Then, the caretaker turns the two side coil portions 12 inward so as to enclose the chest of the subject and connect the side coil portions 12 using the fixing bands 16, but without altering the position of the center coil portion 13. At this time, the distal portions of the side coil portions 12 are placed on the smooth surfaces 23 of the center coil portion 13, and they can slide on the smooth surfaces 23 in response to the tension produced by the fixing bands 16. Accordingly, the side coil portions 12, which are constructed by embedding band-like conductive members inside soft members, can be deformed to match the shape of the chest of the subject and wrapped around the chest of the subject tightly, as shown in FIG. 4.

Next, the caretaker will attach the head coil portion 14 to the head-coil connecting portions 24 on the base coil portion 11. As seen from FIG. 4, when the head coil portion 14 is attached, the ears of the subject come to the positions of the cutaway holes 19 formed in the head coil portion 14. Therefore, the subject can hear ambient sounds without interference and can feel relaxed about the examination.

Surface coils to be discussed later are formed inside the side coil portions 12 at portions close to the center coil portion 13 and around the cutaway holes 18, protruding in the direction of the shoulders and the direction of the waist. Those portions of the side coil portions 12 where the surface coils are not located are cut away. The subject can therefore put his or her arms out through the cutaway portions loosely, thus reducing the awkwardness of putting the probe on. The coils that are formed to protrude in the direction of the shoulders and the direction of the waist can provide an image over a wide range.

Referring now to FIG. 5, a description will be given of how to deform the above-described side coil portions 12 to match the shape of the chest of the subject and wrap them around the chest of the subject tightly.

As shown in FIG. 5, the stepped center portion of the center coil portion 13 that follows the smooth surfaces 23 thereof has a total width of 60 mm, 30 mm in either direction from the center indicator portion 20, and the smooth surface 23 that constitutes the slide mechanism on one side has a width of 75 mm. The distal end portion of each of the two side coil portions 12 can move within a range of the 75-mm width on the smooth surface 23. Accordingly, the inner circumferential length, that is formed by the base coil portion 11, the two side coil portions 12 and the center coil portion 13, can be adjusted within a range of 150 mm. This state is illustrated in FIG. 5. Therefore, the side coil portions 12 can be deformed to match the size of the chest of the subject and be wrapped around the chest of the subject tightly.

As mentioned above, the body probe according to the embodiment of the invention is designed in such a way that a set of one center coil portion 13 and two side coil portions 12 can absorb a difference of 150 mm in the circumferential length of the chest of the subject and the side coil portions 12 can be deformed and put around the chest of the subject tightly. To absorb a difference in the circumferential length of the chest of a larger subject, another center coil portion 13 of a different width size should be prepared. This can allow the body probe of the invention to cope with all types of subjects from a small-sized Japanese person to a large-sized European person.

In case of the conventional cylindrical body probe, at least three types of body probes, large, intermediate and small ones, need to be prepared. By way of contrast, the body probe according to the embodiment of the invention can be used for all types of subjects of different builds by merely preparing two types of center coil portions 13.

FIG. 6 is a diagram illustrating another means for fitting the center coil portion on the subject. In FIG. 6, the probe includes a fixing belt 16, and the other structural elements, which are not given reference symbols, are the same as those explained above with reference to FIGS. 1A, 1B, 2, 3, 4 and 5.

The body probe according to the embodiment of the invention that has already been discussed with reference to FIGS. 1A, 1B, 2, 3, 4 and 5 is designed in such a way that the side coil portions 12 and the center coil portion 13 are fixed in close contact with a subject by use of the fixing bands 16 provided on the side coil portions 12. By way of contrast, the example shown in FIG. 6 is designed in such a way that the fixing belt 16' is attached to the sides of the base coil portion 11. The body probe is attached to the subject first placing the center coil portion 13 on the chest of the subject, then securing the center coil portion 13 on the chest of the subject using the fixing belt 16', and then connecting the side coil portions 12 to the center coil portion 13 in the same way as has been discussed in the foregoing description.

According to the example shown in FIG. 6, the side coil portions 12 have only to be connected to the center coil portion 13 after the center coil portion 13 is secured on the chest of the subject using the fixing belt 16'. The work of attaching the body probe to the subject becomes easier than the work involved in securing the side coil portions 12 and the center coil portion 13 together in close contact with the subject merely by means of the fixing bands 16 in the body probe that has already been described with reference to FIGS. 1A, 1B, 2, 3, 4 and 5. This feature can reduce the burden on the caretaker.

The foregoing description has been directed to an embodiment of a body probe for MRI according to the invention. A description will now be given of the shapes of coils formed in the individual coil portions that have already been discussed.

Figure 7A:
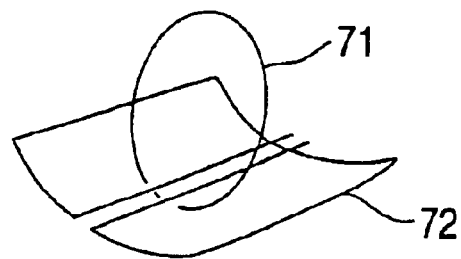
FIGS. 7A and 7B are diagrams illustrating the basic shapes of coils formed in individual coil portions according to the embodiment of the invention and the shape of a coil formed in a head coil portion.
Figure 7B:
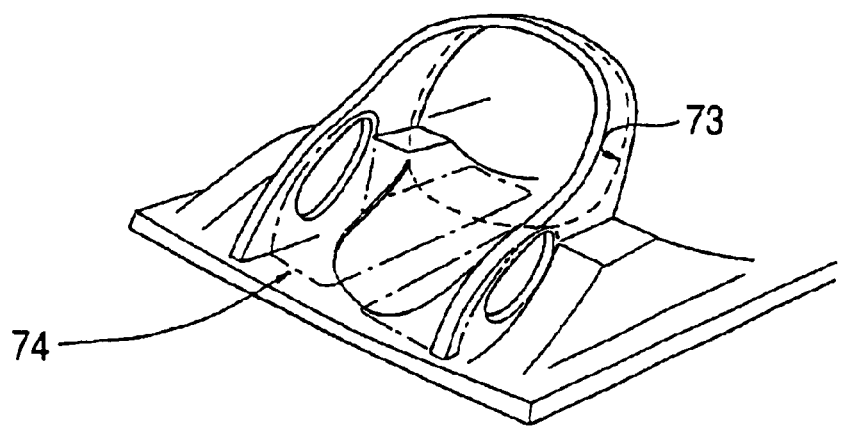
Figure 9:
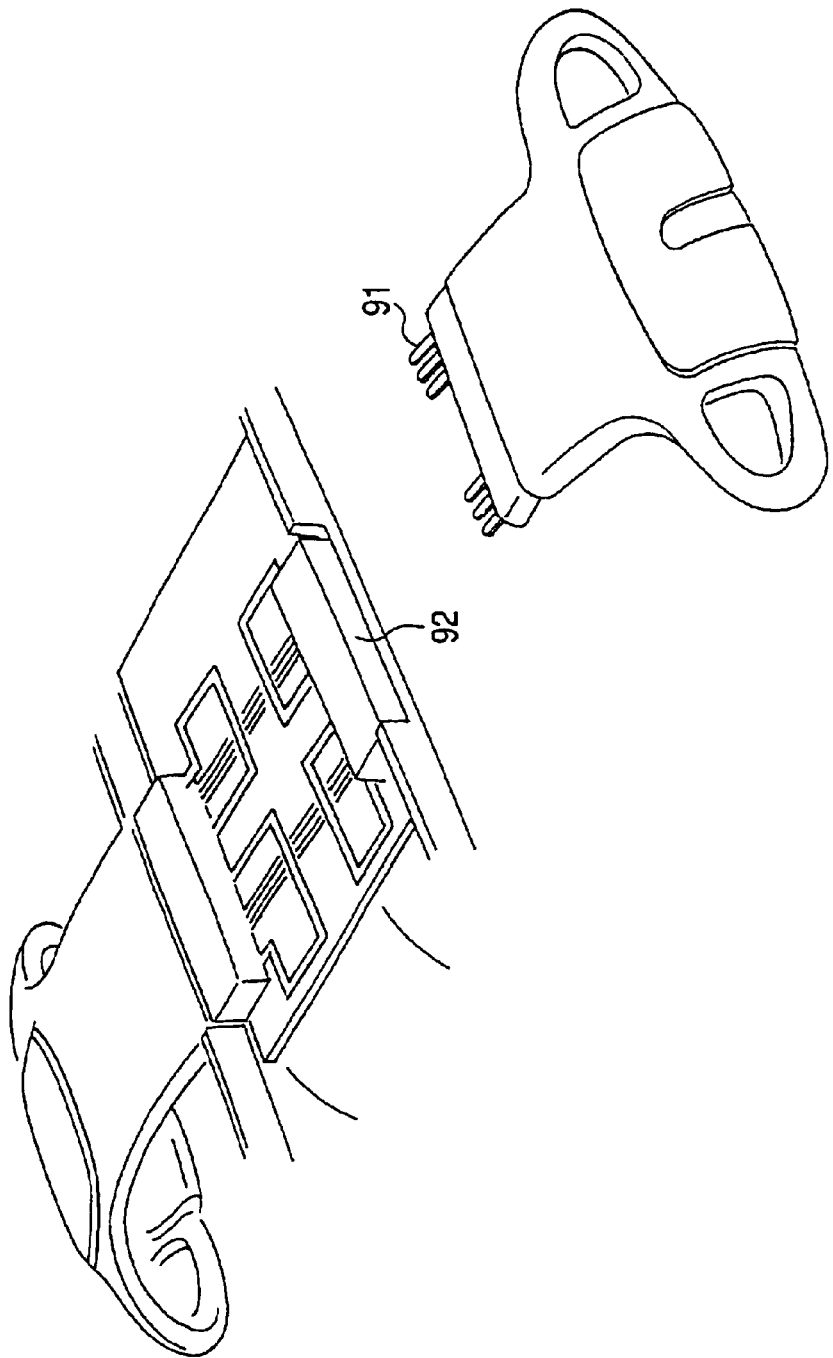
FIG. 9 is a perspective view illustrating the shape of a coil formed in a base coil portion.
Figure 10:
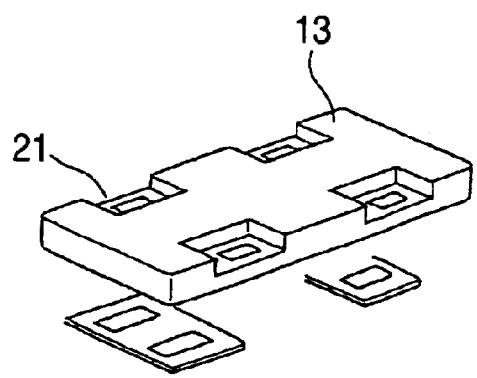
FIG. 10 is a perspective view illustrating the shape of a coil formed in a center coil portion and the structure of a cable connector.
Figure 11A:
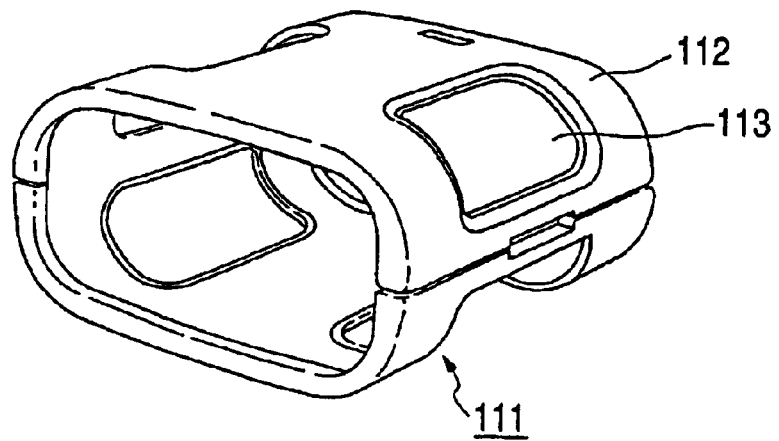
FIGS. 11A and 11B are perspective view illustrating one structural example of a body probe for MRI according to the related art.
Figure 11B:
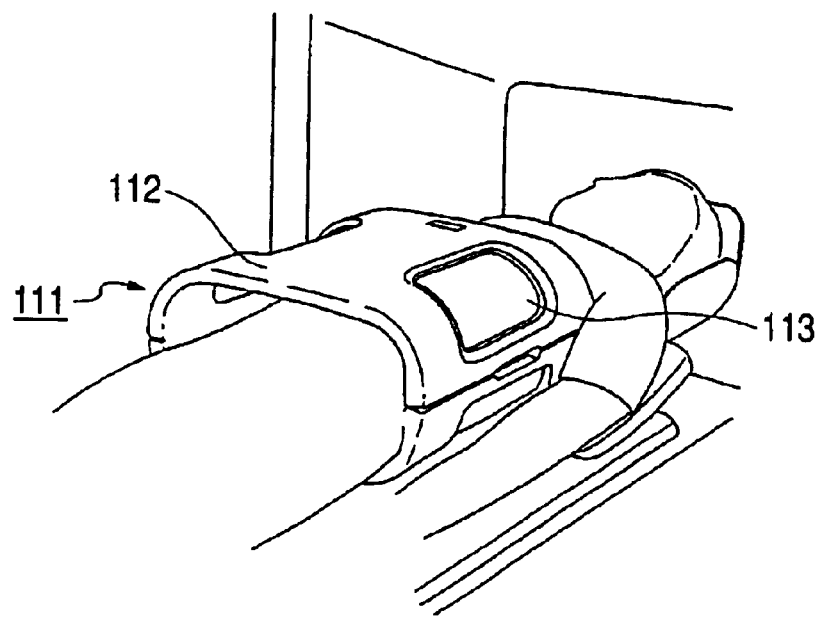
Figure 12:
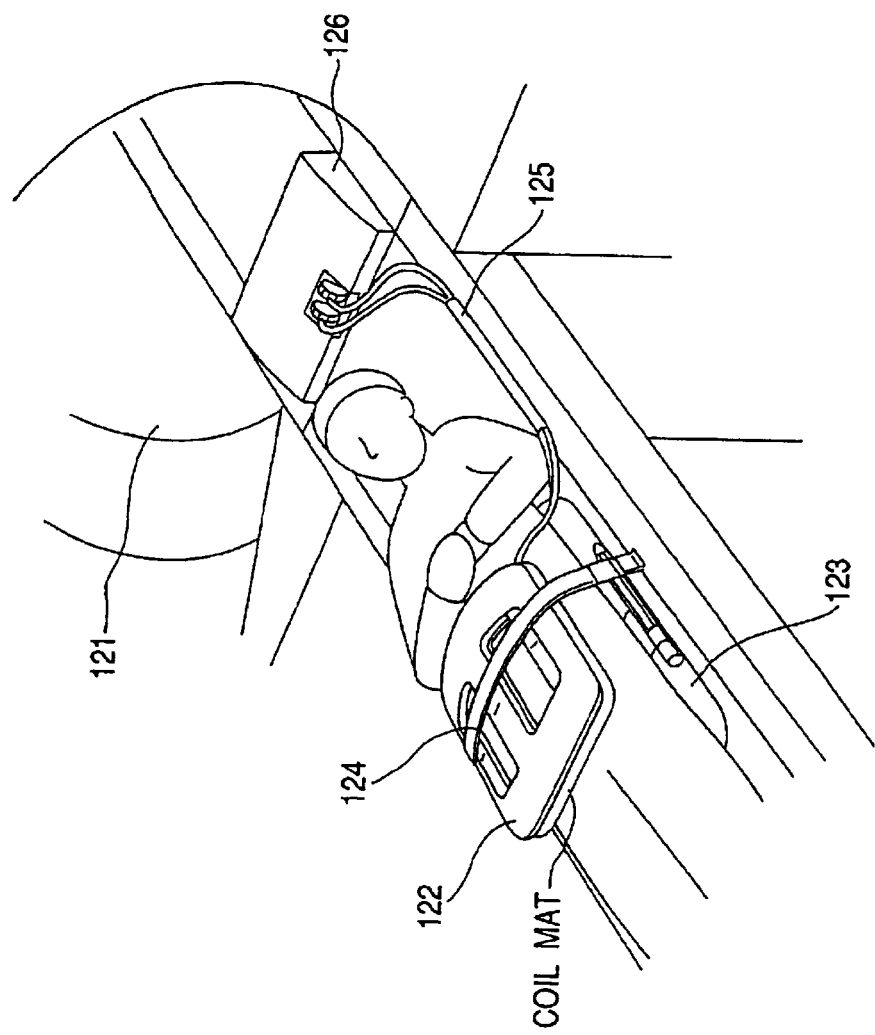
FIG. 12 is a perspective view illustrating another structural example of the body probe for MRI according to the related art.

FIGS. 7A and 7B are diagrams illustrating the basic shapes of coils formed in the individual coil portions according to the invention and the shape of the coil formed in the head coil portion. FIG. 8 is a diagram illustrating the shape of the coil formed in the side coil portion, and FIG. 9 is a diagram illustrating the shape of the coil formed in the base coil portion. FIG. 10 is a diagram illustrating the shape of the coil formed in the center coil portion and the structure of the cable connector. In the drawings, there is a solenoid coil 71, a surface coil 72, a solenoid coil 73 for cervical vertebrae, a surface coil 74 for the head, a solenoid coil 81 for lumbar vertebrae, a solenoid coil 82 for thoracic vertebrae, a surface coil 83 for lumbar vertebrae, a surface coil 84 for thoracic vertebrae, and connectors 91 and 92.

According to the invention, as shown in FIG. 7A, the combination of both the solenoid coil and the surface coil is used in picking up the image of a subject's part of interest. The solenoid coil 71 is formed in a loop and is laid out to surround the subject's part to be picked up. The surface coil 72 is formed in the shape of the letter "8" in such a way as to be extendible in a planar pattern in the coil portion. The surface coil 72 is laid along the subject's part to be picked up.

As shown in FIG. 7B, the cervical-vertebrae solenoid coil 73 for picking up the image of the cervical vertebrae is provided in the bridge that is located in the head coil portion 14 at a position close to the neck of the subject. The cervical-vertebrae solenoid coil 73 is connected inside the base coil portion 11 via unillustrated connectors provided in the head-coil connecting portions 24, so that the entire solenoid coil 73 is formed in a loop. The head surface coil 74 is laid around each cutaway hole 19 formed in the head coil portion 14. The head surface coil 74, like the solenoid coil 73, is connected inside the base coil portion 11 via an unillustrated connector provided in the associated head-coil connecting portion 24, so that the entire solenoid coil 73 is formed in the shape of the letter "8". That internal part of the base coil portion 11 which constitutes a part of the head surface coil 74 has a shape that is elongated toward the associated shoulder.

As shown in FIG. 8, the lumbar-vertebrae solenoid coil 81, the thoracic-vertebrae solenoid coil 82, the lumbar-vertebrae surface coil 83 and the thoracic-vertebrae surface coil 84 are arranged inside each side coil portion 12. The coils 81 and 82 are used to pick up the images of the lumbar vertebrae and thoracic vertebrae. As in the case of the head coil portion 14, the solenoid coils 81 and 82 are connected inside the base coil portion 11 and the center coil portion 13 to form loops and the surface coils 83 and 84 are connected inside the base coil portion 11 and the center coil portion 13 to form the shapes of the letter "8". That side of each coil which is to be connected to the center coil portion 13 is connected to the connector 26 for connection to the center coil portion 13 via the associated coil cable 17, as has already been explained.

As apparent from the foregoing description, the base coil portion 11 connects the coils provided in the side coil portions 12 and the head coil portion 14 to form solenoid coils and surface coils of desired shapes. As shown in FIG. 9, coil portions which form the individual coils provided in the side coil portions 12 are laid inside the base coil portion 11. The connection to each side coil portion 12 is accomplished via the connector 91 provided at the side coil portion 12 and the connector 92 provided at the base coil portion 11. Though not illustrated, the coil portions that form the individual coils in the head coil portion 14 are likewise laid inside the base coil portion 11.

As shown in FIG. 10, two cable connectors 21 are provided on a single circuit board and are provided in the center coil portion 13 in such a way that two cable connectors 21 are positioned on either side of the center portion of the center coil portion 13 that is designed to have a step thicker than the smooth surfaces 23.

Though unillustrated, the individual coils that constitute the body probe and the coils provided in the head coil portion are connected to the body of the MRI apparatus via cables for acquisition of reception signals, so that an image is produced from the reception signals.

According to the invention, the provision of the coils in separated plural coil portions and the use of the center coil portion facilitate the attachment of the coils to a subject in such a way that the center of each coil is always aligned with the center of the body axis of the subject. According to the invention, each side coil portion is constructed by embedding a flexible coil in a soft member and the position at which the center coil portion is joined to the side coil portions can be slidably adjusted. It is therefore possible to allow the reception coils to be attached to the body of the subject tightly to accommodate any difference in the build of the subject. This can provide high-precision images.

According to the embodiment of the invention, because the slide adjustment can allow the reception coils to be attached to the body of the subject tightly, the coil center does not deviate even when the subject moves. As a result, high-precision images can be obtained. Since the center coil portion 13 has a portion that permits slide adjustment of the side coil portions, preparation of two types of center coil portions of different width sizes can allow the body probe to be used for all types of subjects of different builds.

According to the embodiment of the invention, since cutaway holes are formed in those portions of the individual coil portions where there are no coils laid out and the member for molding the coils is a soft member, such as a rubber-based or urethane based member, it is easy to fit the body probe on the subject, and it is possible to improve the sensation of attachment and the feeling of freedom.

As described above, the invention can provide an easy-to-use body probe for MRI which is easily attached to various types of subjects to be examined and does not suffer image degradation, and an MRI apparatus which uses this probe.

A body probe for MRI according to the invention and an MRI apparatus using the probe can be effectively used in the medical equipment industry.

What is claimed is:

1. A body probe for MRI having reception coils for picking up an image for use in an MRI apparatus, said reception coils being provided in a center coil portion and two side coil portions, wherein slide mechanisms of said side coil portions are provided at joint portions between said center coil portion and said side coil portions.

2. The body probe for MRI according to claim 1, wherein smooth surfaces are formed on both right and left sides of said center coil portion and constitute said slide mechanisms.

3. The body probe for MRI according to claim 1, wherein a bottom surface of said center coil portion is curved.

4. The body probe for MRI according to claim 1, wherein an indicator indicating a center of a center coil is provided at a center of a top surface of said center coil portion.

5. The body probe for MRI according to claim 4, wherein said indicator indicating said center of said center coil is a groove, a projection or a line drawn in color different from a color around said line.

6. A body probe for MRI having reception coils for picking up an image for use in an MRI apparatus, said reception coils being provided in a center coil portion, a pair of side coil portions and a base coil portion, and side-coil connecting portions provided on both sides of said base coil portion, wherein said pair of side coil portions are attached by said side-coil connecting portions to said base coil portion so as to be movable at an arbitrary angle with respect to said base coil portion, and said center coil portion enables coupling of said pair of side coil portions together.

7. The body probe for MRI according to claim 6, wherein said base coil portion is provided with a head holder for holding the head of a subject to be examined.

8. The body probe for MRI according to claim 6, wherein said center coil portion, said pair of side coil portions and said base coil portion are constructed independently of one another.

9. The body probe for MRI according to claim 6, wherein said side coil portions are constructed by embedding a flexible coil in a soft member.

10. The body probe for MRI according to claim 6, wherein said side coil portions are provided with cutaway holes at portions where there are no coil portions.

11. An MRI apparatus comprising a body probe having reception coils for picking up an image, said reception coils being provided in a center coil portion, a pair of side coil portions and a base coil portion, and side-coil connecting portions provided on both sides of said base coil portion, wherein said pair of side coil portions are attached by said side-coil connecting portions to said base coil portion so as to be movable at an arbitrary angle with respect to said base coil portion, and said center coil portion enables coupling of said pair of side coil portions together.

* * * * *